United States Patent [19]

Nicholas

[11] 4,263,586

[45] Apr. 21, 1981

[54] PRESSURE OPERATED ELECTRIC SWITCH AND ALARM SYSTEM USING SUCH SWITCH

[76] Inventor: Noel Nicholas, 6, Verona Villas, O'Connell Ave., Limerick, Ireland

[21] Appl. No.: 907,461

[22] Filed: May 19, 1978

Related U.S. Application Data

[63] Continuation-in-part of Ser. No. 826,957, Aug. 22, 1977, abandoned.

[30] Foreign Application Priority Data

Aug. 26, 1977 [IE] Ireland ................. 1867/77

[51] Int. Cl.³ ............................................. G08B 13/14
[52] U.S. Cl. ................................. 340/568; 340/573; 340/666; 200/85 R
[58] Field of Search ............... 340/568, 665, 666, 686, 340/573; 200/85 R, 86 R, 86 A, 67 D, 67 DA

[56] References Cited

U.S. PATENT DOCUMENTS

| | | | |
|---|---|---|---|
| 1,758,546 | 5/1930 | Wantmann | 340/568 |
| 2,458,192 | 1/1949 | Niles | 340/568 |
| 2,818,477 | 12/1957 | Gollhofer | 200/85 R |
| 3,656,141 | 4/1972 | Hill | 340/666 |
| 3,824,536 | 7/1974 | Cherico | 200/85 R |
| 3,852,736 | 12/1974 | Cook et al. | 340/666 |
| 3,961,201 | 6/1976 | Rosenthal | 340/666 |

*Primary Examiner*—John W. Caldwell, Sr.
*Assistant Examiner*—Donnie L. Crosland
*Attorney, Agent, or Firm*—Sughrue, Rothwell, Mion, Zinn and Macpeak

[57] ABSTRACT

A pressure operated electrical switch and an alarm system for use in hospitals and nursing homes. The switch is constructed such that a force is applied to a pressure plate therein, and once the load is reduced below a predetermined value the pressure plate will move under spring influence to close/open a microswitch or electrical contact means. The normal force applied to the pressure plate is the load on the leg of a hospital bed when occupied. If the bed occupant gets out of the bed the load on the pressure plate is reduced below the predetermined value and the consequent movement of the pressure plate opens/closes the switch means to actuate the alarm.

6 Claims, 22 Drawing Figures

PRESSURE OPERATED ELECTRIC SWITCH AND ALARM SYSTEM USING SUCH SWITCH

This application is a continuation-in-part of my co-pending Application Ser. No. 826,957, for PRESSURE OPERATED ELECTRIC SWITCH AND ALARM SYSTEM USING SUCH SWITCH, filed Aug. 22, 1977, now abandoned.

The present invention relates to a pressure-operated electric switch and an alarm system using the switch.

According to the present invention there is provided a pressure-operated electric switch for use in conjunction with a hospital bed and adapted for insertion under one leg of the bed to signal the absence of a patient therein, the electric switch comprising a portable housing having a base, a generally horizontal pressure plate mounted in the housing for vertical movement relative to the base, the pressure plate having an upper surface, spring means extending upwardly from a supporting surface in the housing below the pressure plate and biasing the pressure plate upwards, at least a portion of the upper surface of the pressure plate being exposed to allow the opposition to the spring means, means for locating the lower end of a leg of a bed in overlying relationship to said pressure plate, first and second contact means mounted inside the housing and adapted for actuation by movement of the pressure plate whereby the first and second contact means are brought into engagement at a selected height of the pressure plate above the base, and means to adjust the height of the pressure plate at which the contact means are brought into engagement.

The application of the switch according to the invention is to give an alarm to a nurse or other person minding a patient likely to get out of bed. In this application, the switch is acted on by a leg of the bed and is adjusted such that when the bed is occupied by the patient, the pressure acting on the switch is sufficient to maintain the switch, for example, the open position whereas when the bed becomes unoccupied the switch contacts move to the closed position to give an alarm. The alarm may be audible and/or visible, e.g. it may comprise a bell and/or a light.

Particular embodiments of the pressure-operated electric switches and alarm systems incorporating switches, are hereinafter described with reference to the accompanying drawings, in which:

FIG. 4b is a plan view of the switch of FIG. 4a;

FIG. 4c is a side elevation of the switch of FIG. 4a;

FIG. 4d is a plan view of the pressure plate of the switch of FIG. 4a;

FIG. 4e is an end elevation of the switch of FIG. 4a;

FIG. 4f is a plan view of the spring mounting block of the switch of FIG. 4a;

FIG. 5b is an underneath plan view of the switch of FIG. 5a;

Figure 1:
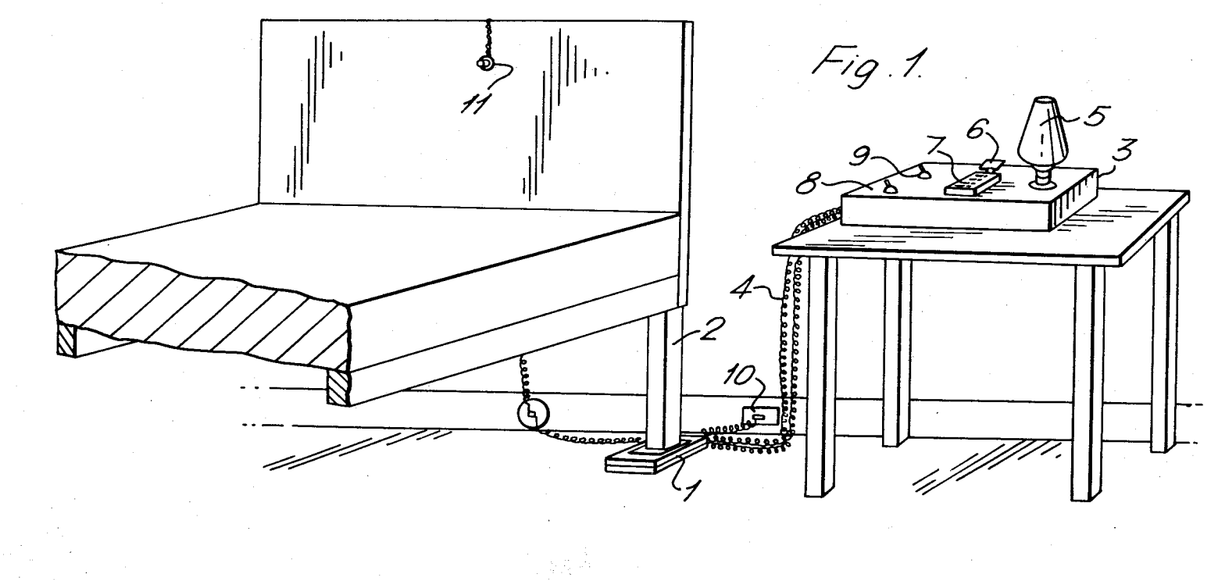
FIG. 1 is a schematic diagram of a switch and alarm circuit as installed in use so as to be operable by the leg of a bed.

As shown in FIG. 1, a pressure-operated electric switch 1 is positioned below the end of a bed leg 2 and is connected to an alarm circuit 3 by pairs of wires 4.

The alarm circuit 3 includes a light 5, a bell 6, a battery 7 for energising the bell circuit, a switch 8 in the light circuit and a switch 9 in the bell circuit. The light circuit is energised from a main supply socket outlet 10. Normally, the switches 8, 9 are in the closed position but may be opened to interrupt the alarm. A push button switch 11 for use with the main house call bell is provided mounted on the bedhead. The circuit diagram of the alarm circuit is shown in FIG. 2.

Figure 2:
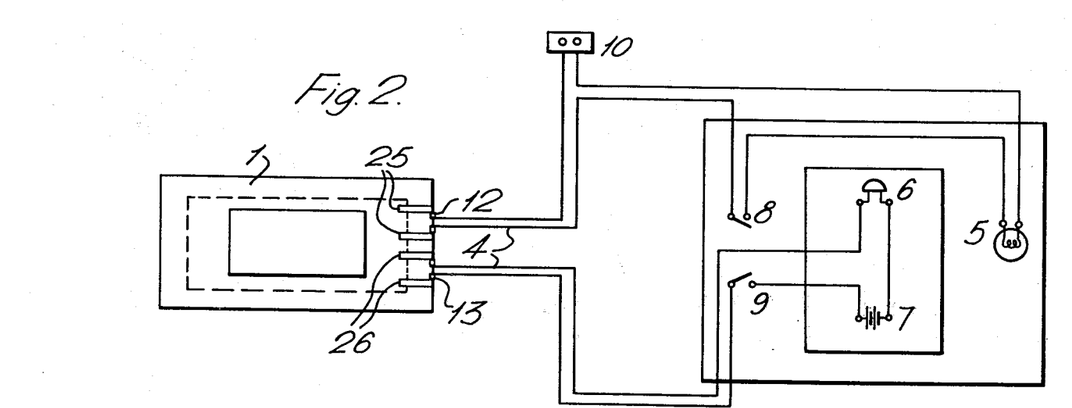
FIG. 2 is a circuit diagram of the switch and alarm circuit of FIG. 1.
Figure 7:
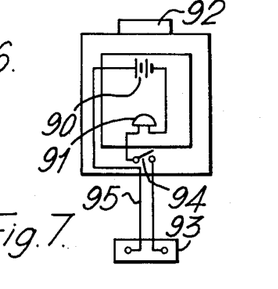
FIG. 7 is a portable bell arrangement which may be used in conjunction with the pressure-operated switch.
Figure 9:
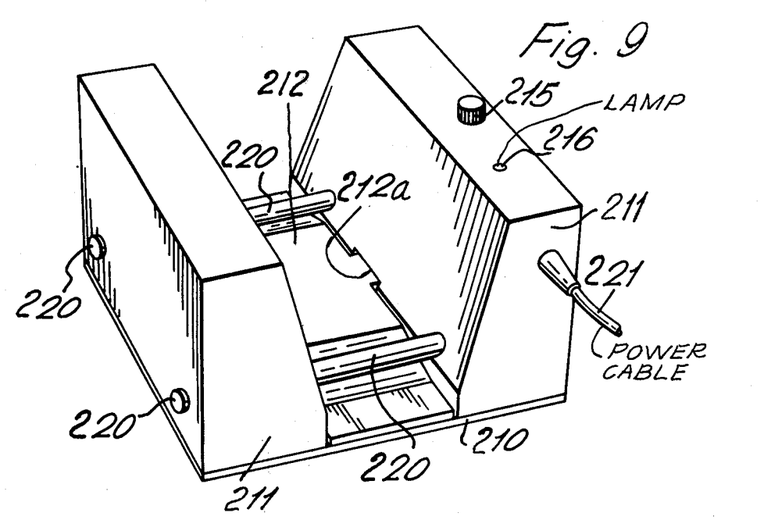
FIG. 9 is a perspective view of still another form of switch.
Figure 10:
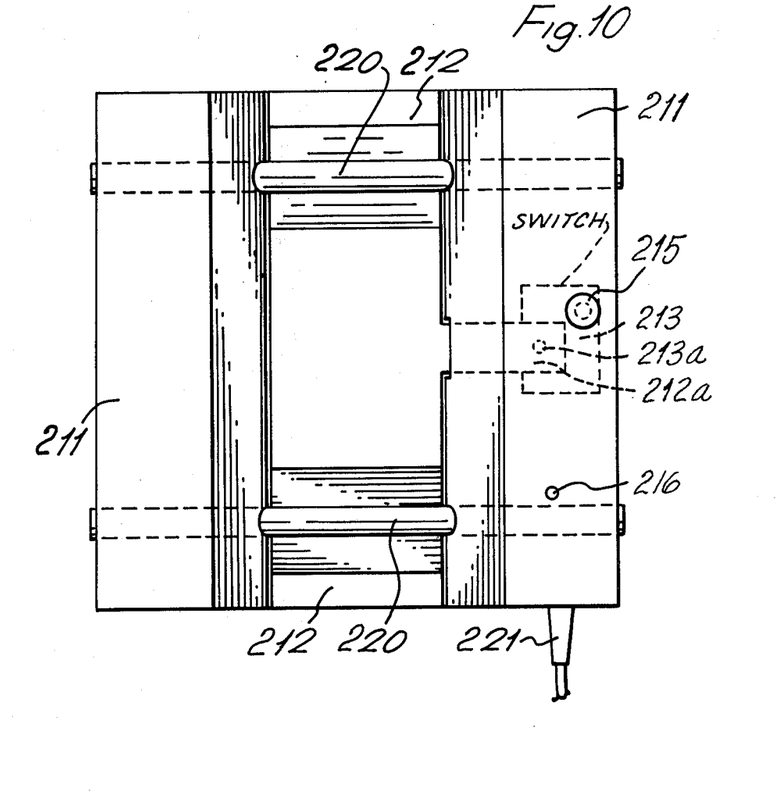
FIG. 10 is a plan view of the switch of FIG. 9.
Figure 11:
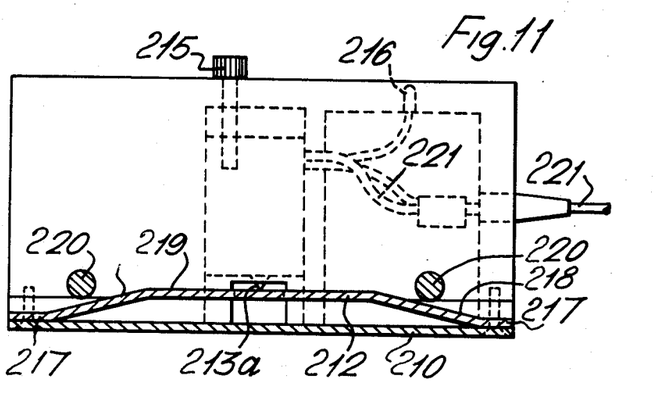
FIG. 11 is a transverse vertical sectional view of the switch of FIG. 9.
Figure 12:
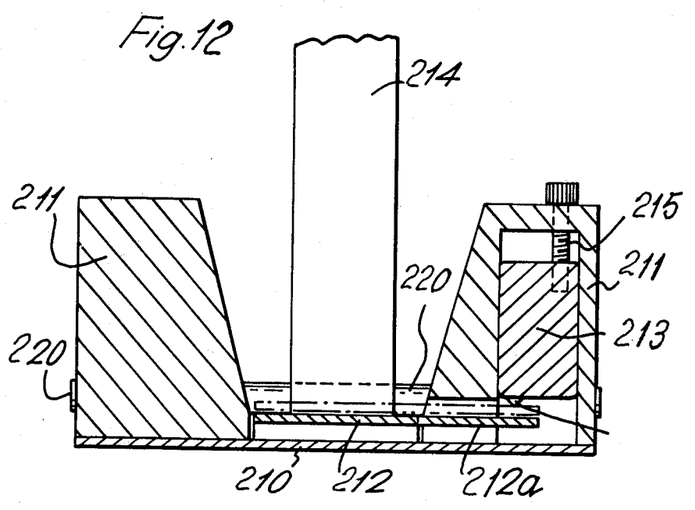
FIG. 12 is a longitudinal vertical sectional view of the switch of FIG. 9 with a wheel of a hospital bed shown in position on the switch.

The connection of the pairs of wires 4 to the switch 1 are preferably made by plug-and-socket connectors 12, 13, FIG. 2. Thus, a portable bell as shown in FIG. 7 may be plugged into the switch, or, when the alarm system is used in a house, the main house bell may be connected to the switch.

Figure 3A:
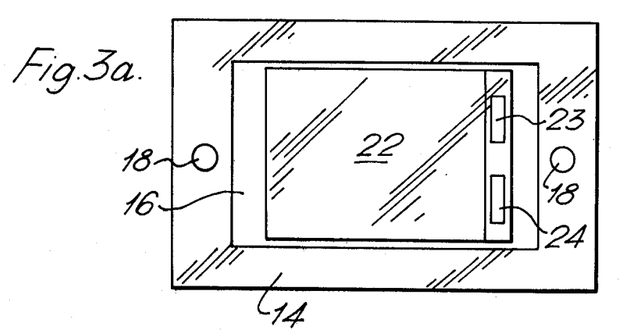
FIG. 3a is a plan view of the base of the switch of FIG. 1.
Figure 3B:
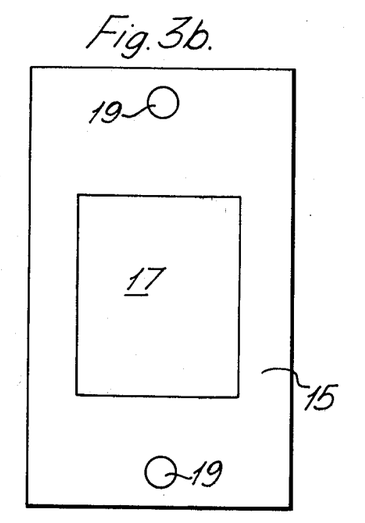
FIG. 3b is a plan view of the lid of the switch of FIG. 1.
Figure 3C:
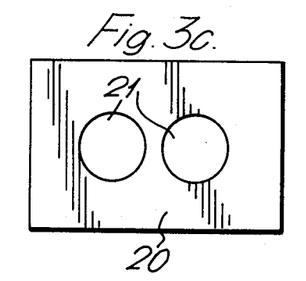
FIG. 3c is a plan view of a housing for the main pressure springs of the switch of FIG. 1.

The switch 1 comprises a hollow box-like base 14, FIG. 3a, with a central cavity 16, and an overlying lid 15, FIG. 3b, which together with the base forms a hollow housing. The lid 15 has an aperture 17 for receiving the lower end of the bed leg 2. The lid 15 has depending side walls which surround the base 14 and is supported on the base by a pair of coiled springs (not shown) surrounding screw-threaded socket bolts or studs 18 upstanding from the base and extending through holes 19 in the lid. The upper ends of the of the springs abut the underside of the lid and the ends of the studs 18 extending through the lid holes 19 receive wing nuts bearing on the lid surface through washers.

The cavity 16 receives a spring housing 20 having apertures 21 for accommodating a pair of main coiled springs (not shown) for taking the load exerted by the bed leg. The housing 20 may be in the form of a block having a metal plate on its underside for closing the ends of the apertures 21. The upper ends of the main springs support a metal pressure plate 22, FIG. 3d, which is engaged on its upper surface by the bed leg 2 extending through aperture 17. The upper surface of the plate 22 carries a pair of bridging switch contacts 23, 24 which are insulatingly mounted on the plate. When the pressure exerted on the plate 22 by the leg 2 falls below a predetermined value, the plate is raised by the main springs so that the contacts 23, 24 bridge corresponding pairs of strip-type contacts 25, 26 mounted on the underside of the lid, FIG. 2. The contact pairs 25, 26 are connected, respectively, in the light and bell circuits by the plug-and-socket connectors 12, 13 and thus both the light and bell are energised to give the alarm.

Figure 3D:
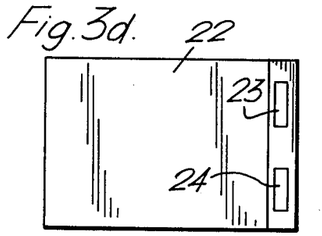
FIG. 3d is a plan view of the pressure plate of the switch of FIG. 1.
Figures 3E, 8:
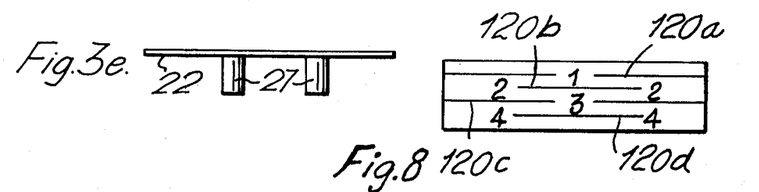
FIG. 3e is an end elevational view of the pressure plate of FIG. 3d.
FIG. 8 is a side elevational view of a switch base showing the pressure-setting lines facilitating adjustment of the switch operating pressure.

To impart additional stability to the pressure plate 22 it may be provided on its underside with studs 27 which extend through the main coiled springs, FIG. 3e.

The pressure required on the plate 22 to separate the contacts 23, 24 from the contacts 25, 26 respectively, may be varied by adjusting the wing nuts on the socket bolts or studs 18 to vary the vertical spacing between the lid 15 and the base 14. Also, the pressure required to separate the contacts may be increased by inserting a packing plate between the base of the spring housing 20 and the floor of the base-cavity 16.

In one construction of the switch 1, the base 14, cover 15 and spring housing 20 are of wood, but any other suitable material may be used.

Referring now to the switch construction shown in FIGS. 4a to 4f, the switch comprises a base 30 with a central cavity 31 receiving a spring mounting block 32 having a pair of apertures 33 accommodating the lower ends of main springs 34. The upper ends of the springs 34 abut a pressure plate 35 and urge the plate towards the inner surface of a lid 36 having a central aperture 37 for receiving the leg of a bed. The block 32 is seated in a metal tray 38, and studs 39, 40 respectively are provided on the plate 35 and the tray 38 for stabilising the springs 34. The lid 36 is supported on the base 30 by screw-threaded bolts 41 co-operating with screw-threaded socket 42 secured to the base, the upper ends of the bolts having reduced neck portions 43 co-operating with brackets 44 sunk into the top surface of the lid. The end of each bolt 41 has a knob 45 so that the bolts may be rotated to adjust the distance of the base from the lid and thus the pressure required to operate the switch. A pointer 46 on the knob registers on a circular scale 47 (FIG. 4b) provided on the lid. A further adjustment of the operating pressure may be obtained by inserting one or more packing plates beneath the tray 38. To permit rotating the knobs by e.g., a screwdriver, they may be provided with a slot. The screw-threaded sockets 42 are secured to the base by brackets 49 sunk into the base, the brackets 49 being of square cross-section for preventing rotation on the base.

To maintain even pressure adjustment between the two knobs 45, the base is provided externally with horizontal indicator lines 46a, b and c (FIG. 4c) for registering with the lower edge of the lid; also, the lines are indicative of the pressure setting. Thus line 46a indicates low pressure, line 46b medium pressure and line 46c high pressure.

Figure 4A:
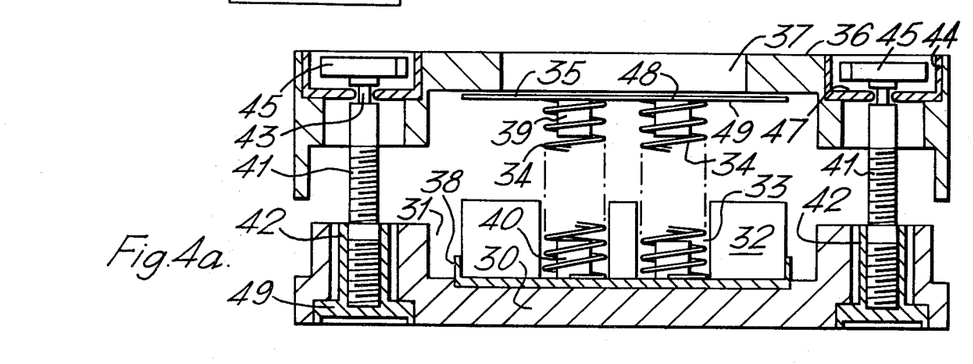
FIG. 4a is a cross-sectional view of a second embodiment of the pressure-operated switch.
Figure 4B:
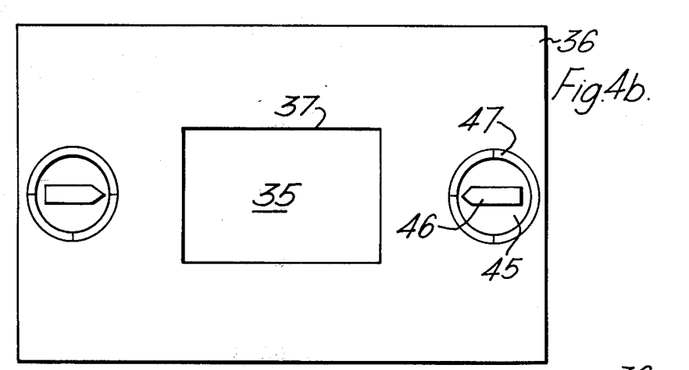
Figure 4C:
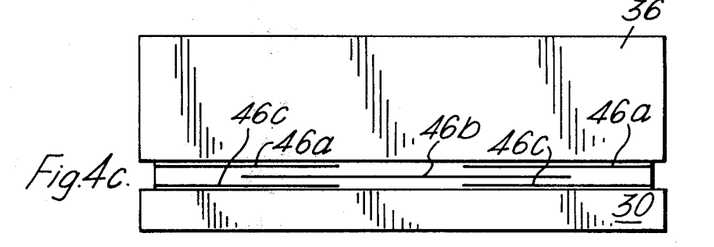
Figure 4D:
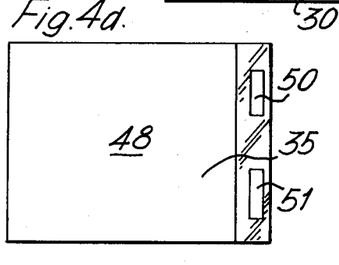
Figure 4E:
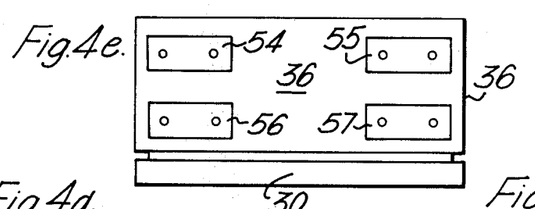
Figure 4F:
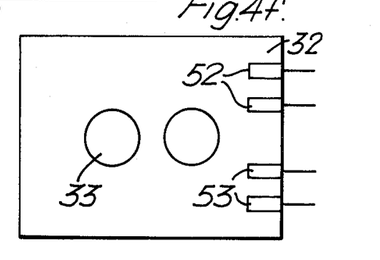

The pressure plate 35, FIG. 4d, insulatingly carries on each of its upper and lower surfaces 48, 49, two bridging contacts 50, 51. FIG. 4d shows the two bridging contacts on the upper surface 48 and a similar pair of contacts, not shown, are provided on the lower surface 49. The contacts 50, 51 on the upper surface serve to bridge corresponding pairs of fixed contacts (not shown) provided on the upper surface of the lid when the pressure plate 35 is biased by the springs 34 against the lid as shown in FIG. 4a. Two further pairs of contacts 52, 53, FIG. 4f, are provided on the upper surface of the block 32 and these are bridged by the bridging contacts on the underside of the pressure plate when sufficient force is applied to the plate to move it downwardly against the spring pressure. The two pairs of contacts carried by the lid are connected by wires to respective ones of the upper two plugs 54, 55 of four plugs 54–57, flush-mounted in one end of the lid 36, FIG. 4e, and the two pairs of contacts 52, 53 carried by the block 32 are similarly connected by wires to the lower plugs 56, 57.

The left-hand plugs 54, 56 serve for connection to the alarm bell circuit and the right-hand plugs 55, 57 serve for connection to the light circuit described previously with reference to FIG. 2. Thus, by inserting sockets into the lower or upper plugs, a choice may be made as to whether the alarm is to be given and the light energised either when the force acting on the pressure plate is increased or when it it decreased.

Figure 5A:
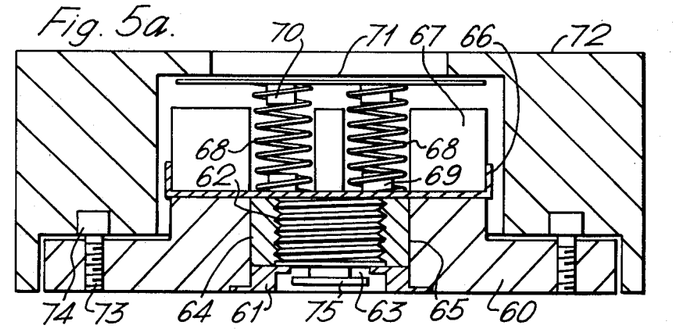
FIG. 5a is a cross-sectional view of a third embodiment of the pressure-operated switch.
Figure 5B:
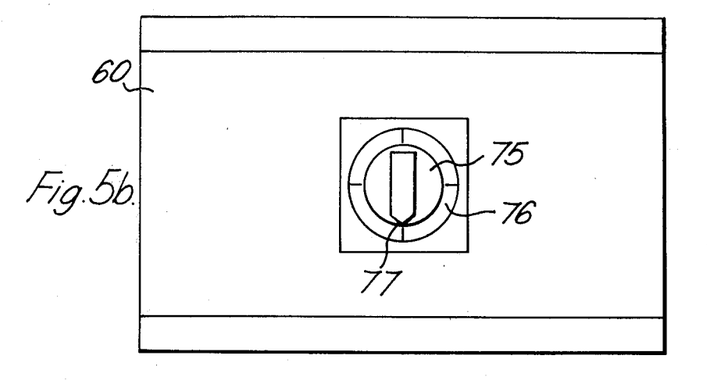

In the embodiment of the pressure-operated switch shown in FIGS. 5a and 5b, the switch base 60 has a central aperture 65, in which an annular bracket 61 is secured rotatably supporting a screw-threaded bolt 62, by co-operating with a reduced neck portion 63 of the bolt. A screw-threaded socket 64 in threaded engagement with the bolt 62, is slidably guided in the base aperture 65 and is attached to the underside of a metal tray 66, receiving a spring mounting block 67. The pair of springs 68 are stabilized by studs 69 on the tray 66 and studs 70 on a pressure plate 71. A lid 72 is attached to the base 60 by bolts 73, co-operating with sockets 74. Pairs of bridging contacts, not shown, are provided on the upper-and lower surfaces of the pressure plate similar to those of FIG. 4d, and pairs of contacts, not shown, are provided on the underside of the lid 72 and on the spring mounting block 67, similar to those described with reference to FIGS. 4a and 4f. Also, the end of the cover 72 has four sockets arranged similarly to those shown in FIG. 4e. In this embodiment the switch operating pressure is adjusted by rotation of the single bolt 62 by means of a knob 75, this action causing raising or lowering of the tray 66 relative to the lid 75. The knob 75 has a pointer 77 registering with a scale 76.

Figure 6:
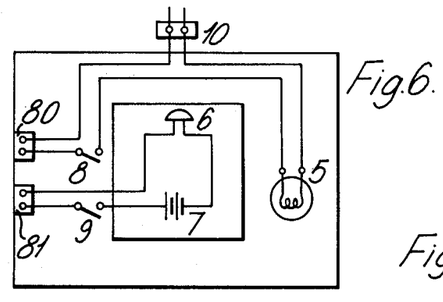
FIG. 6 is a modification of the bedside alarm circuitry shown in FIG. 2.

The bedside control panel circuitry shown in FIG. 6 is similar to that shown in FIG. 2 but includes sockets 80, 81 to enable connection to the made with the pressure-operated switch by means of flexible cables having plug at each end, one end being inserted into the switch and the other end being plugged into the control panel.

FIG. 7 shows a portable bell 91 in a case having a carrying handle 92, the bell having a battery 90 controlled by a switch 94 and being provided with a flexible cable 95 having a plug 93 for connection to the pressure-operated switch.

FIG. 8 is a side elevational view of a base of a pressure-operated switch similar to the base of the switch of FIGS. 4a to 4f but having four pressure-setting indicator lines 120a, b, c and d, the line 120a corresponding to the lowest pressure and the line 120d to the highest pressure. The lines may be provided on each of the four sides of the base.

The preferred embodiments of the present invention described above describe a pressure operated electrical switch which incorporates helical springs for taking the load exerted by the bed leg when the invention is in use in an alarm system in use in hospitals. The present invention also envisages as a further embodiment a design of switch housing which accommodates external to the housing a leaf spring centrally mounted on the base and adapted under the influence of a load i.e. the load exerted by the bed leg, for vertical movement relative to said base. The leaf spring acts not only as a spring but in the context of the present invention also acts as the pressure plate. A small strip of metal, which is operatively connected to the leaf spring, acts as a level indicator and the strip of metal co-operates with a microswitch i.e. first and second contact means housed within the casing.

This embodiment is particularly adapted to accommodate a castor wheel i.e. a wheel at the bottom of a bed leg, by having the leaf spring/pressure plate openly centrally mounted on the base and walled in on its two sides by the switch casing which houses the switch mechanism which responds to the movement of the level indicator attached to the leaf spring. In this manner the castor wheel is positively located in a guideway formed by side walls formed by the casing and the leaf spring mounted within the guideway so formed acts not only as the spring means and pressure plate of the invention but also as a locating ramp for the castor wheel.

The switch of FIGS. 9-12 comprises a molded plastics housing including a base 210 and side walls 211. A steel pressure plate 212 is mounted on the base 210 with the pressure plate 212 being a suitably shaped leaf spring adapted for vertical flexing movement relative to the base 210. One of the side walls 211 locates and accommodates a switch mechanism 213 which co-operates with the pressure plate 212 to open/close an electric circuit to deactuate/actuate an alarm system.

The vertical flexing movement of the pressure plate 212 relative to the base 210 is determined by the force exerted upon the exposed face of the central portion of plates 212 such as by a wheel 214 of a hospital bed. If a patient is in the bed the force on the plate 212 holds a tongue 212a of the plate 212 out of contact with a switch 213. If the patient leaves the bed, the resultant reduction in weight and hence the force on the plate 212 allows the plate 212 to flex upwardly with the tongue 212a engaging the contact 213a of the switch 213 to close an electric circuit and actuate an audible and/or visual alarm.

The vertical position of the switch 213 within the respective side wall 211 of the housing is adjustable by means of an adjustment screw 215. Since the leaf spring pressure plate 212 cannot be varied at will adjustment of the switch position allows the device to cater for varying weights of patients in a bed.

A visual indicator means is provided comprising a light 216 operatively connected to the switch 213. In use the light 216 operates when the switch 213 is closed. Accordingly, a nurse setting the alarm adjusts the switch position—with the patient in the bed—until the light 216 goes out. This means the switch contact 213a and the plate tongue 212a are just separated and the device correctly set. The light 216 also serves to confirm to the nurse—as she sets the device—that it is operative. If no light shows then the device may be defective.

The leaf spring pressure plate 212 has its side edges 217 in firm contact with the base 210 and it is inclined as at 218 to a flat plateau 219. The inclined portions 218 serve not only to permit the pressure plate 212 to function as a leaf spring but to also form ramps for rolling the hospital bed wheel 214 on the flat central portion or plateau 219. The side walls 211 are bridged by steel rods 220 which hold the leaf spring pressure plate 212 loosely in position. The steel rods 220 allow adequate vertical movement of the plate 212. The steel rods 220 also act primarily to hold the bed wheel 214 in position in contact with the plateau portion 219 of the leaf spring pressure plate 212.

The power supply to the device is electric and the relevant cables are indicated at 221.

It will be readily appreciated that the alarm system of the present invention has particular application in hospitals and nursing homes. In such use it is desirable and technically feasible using known/conventional electrical and/or electronic components to integrate the alarm system of the present invention with existing nurse calling systems.

I claim:

1. A pressure-operated electric switch for use in conjunction with a hospital bed and adapted for insertion under one leg of the bed to signal the absence of a patient therein, the electric switch comprising a portable housing having a base, a generally horizontal pressure plate mounted in the housing for vertical movement relative to the base, the pressure plate having an upper surface, spring means extending upwardly from a supporting surface in the housing below the pressure plate and biasing the pressure plate upwards, the pressure plate and the spring means being unitary and comprising a single leaf spring mounted on the base, at least a portion of the upper surface of the pressure plate being exposed to allow the application of an external force to the pressure plate in opposition to the spring means, means for locating the lower end of a leg of a bed in overlying relationship to said pressure plate, first and second contact means mounted inside the housing and adapted for actuation by movement of the pressure plate whereby the first and second contact means are brought into engagement at a selected height of the pressure plate above the base, and means to adjust the height of the pressure plate at which the contact means are brought into engagement.

2. A switch as claimed in claim 1, in which the pressure plate comprises a generally horizontal raised portion of the leaf spring and the spring means comprises at least one downwardly inclined portion of the leaf spring which extends outwardly from one side of the raised portion.

3. A switch as claimed in claim 2, wherein said locating means comprises a pair of upstanding side walls of the housing defining therebetween a passageway for a wheel, the leaf spring extending along the length of the passageway with the downwardly inclined portion thereof forming a ramp for the wheel.

4. A switch as claimed in claim 3 wherein the locating means further includes a pair of stop members extending between said side walls across the leaf spring on opposite sides of said pressure plate.

5. A switch as claimed in claim 3, wherein said first and second contact means are embodied in a microswitch.

6. A switch as claimed in claim 5, wherein the adjusting means comprises means for adjusting the height of the microswitch relative to the base.

* * * * *